United States Patent
Takayama et al.

(10) Patent No.: US 11,383,105 B2
(45) Date of Patent: Jul. 12, 2022

(54) PARTICLE BEAM TRANSPORT APPARATUS, ROTARY GANTRY, AND PARTICLE BEAM IRRADIATION TREATMENT SYSTEM

(71) Applicants: KABUSHIKI KAISHA TOSHIBA, Minato-ku (JP); Toshiba Energy Systems & Solutions Corporation, Kawasaki (JP)

(72) Inventors: Shigeki Takayama, Yokohama (JP); Tomofumi Orikasa, Yokohama (JP); Yoshifumi Nagamoto, Yokohama (JP); Takeshi Yoshiyuki, Yokohama (JP)

(73) Assignees: KABUSHIKI KAISHA TOSHIBA, Minato-ku (JP); Toshiba Energy Systems & Solutions Corporation, Kawasaki (JP)

( * ) Notice: Subject to any disclaimer, the term of this patent is extended or adjusted under 35 U.S.C. 154(b) by 719 days.

(21) Appl. No.: 16/346,417

(22) PCT Filed: Nov. 14, 2017

(86) PCT No.: PCT/JP2017/040886
§ 371 (c)(1),
(2) Date: Apr. 30, 2019

(87) PCT Pub. No.: WO2018/092753
PCT Pub. Date: May 24, 2018

(65) Prior Publication Data
US 2019/0255357 A1   Aug. 22, 2019

(30) Foreign Application Priority Data

Nov. 15, 2016 (JP) .............................. JP2016-222689

(51) Int. Cl.
*A61N 5/10* (2006.01)
*H05H 7/04* (2006.01)
(Continued)

(52) U.S. Cl.
CPC .............. *A61N 5/1043* (2013.01); *A61N 2/02* (2013.01); *A61N 2/06* (2013.01); *A61N 5/10* (2013.01);
(Continued)

(58) Field of Classification Search
CPC ...... A61N 5/1043; A61N 5/10; A61N 5/1081; A61N 2/02; A61N 2/06; A61N 2005/1087;
(Continued)

(56) References Cited

U.S. PATENT DOCUMENTS 10,431,418 B1 * 10/2019 Mizushima ............. H01J 37/21
2014/0163301 A1   6/2014 Trbojevic
(Continued)

FOREIGN PATENT DOCUMENTS

EP         2 750 484 A1    7/2014
JP       2007-260222 A    10/2007
(Continued)

OTHER PUBLICATIONS

International Search Report dated Dec. 26, 2017 in PCT/JP2017/040886 filed Nov. 14, 2017.

*Primary Examiner* — Kiet T Nguyen
(74) *Attorney, Agent, or Firm* — Oblon, McClelland, Maier & Neustadt, L.L.P.

(57) ABSTRACT

A particle beam transport apparatus includes a vacuum duct, at least one magnet controller, and a scanning magnet. The vacuum duct is configured such that a particle beam advances through the vacuum duct. The magnet controller is disposed around a bent portion of the vacuum duct and is configured to control an advancing direction or shape of the particle beam. The scanning magnet is disposed on the downstream side of the magnet controller in the advancing direction and is configured to scan the particle beam by (Continued)

deflecting each bunch of the particle beam. The magnet controller includes a deflection magnet configured to deflect the advancing direction of the particle beam along the bent portion and a quadrupole magnet configured to converge the particle beam. The deflection magnet and the quadrupole magnet constitute a combined-function magnet arranged at the same point in the advancing direction.

8 Claims, 7 Drawing Sheets

(51) Int. Cl.
  *G21K 5/04* (2006.01)
  *H05H 7/00* (2006.01)
  *G21K 1/093* (2006.01)
  *A61N 2/02* (2006.01)
  *A61N 2/06* (2006.01)
  *H05H 7/10* (2006.01)

(52) U.S. Cl.
  CPC ............ *A61N 5/1081* (2013.01); *G21K 1/093* (2013.01); *G21K 5/04* (2013.01); *H05H 7/001* (2013.01); *H05H 7/04* (2013.01); *A61N 2005/1087* (2013.01); *H05H 7/10* (2013.01); *H05H 2007/002* (2013.01); *H05H 2007/046* (2013.01); *H05H 2007/048* (2013.01)

(58) Field of Classification Search
  CPC .... A61N 2005/109; G21K 1/093; G21K 5/04; H05H 7/001; H05H 7/04; H05H 7/10; H05H 2007/002; H05H 2007/046; H05H 2007/048
  USPC ........................................ 250/492.3, 396 ML
  See application file for complete search history.

(56) References Cited

U.S. PATENT DOCUMENTS

| | | | |
|---|---|---|---|
| 2014/0187844 | A1 | 7/2014 | Saito et al. |
| 2017/0229281 | A1 | 8/2017 | Furukawa et al. |

FOREIGN PATENT DOCUMENTS

| | | |
|---|---|---|
| JP | 2011-72717 A | 4/2011 |
| JP | 2012-11038 A | 1/2012 |
| JP | 2014-127377 A | 7/2014 |
| JP | 2015-80594 A | 4/2015 |
| JP | 2016-83344 A | 5/2016 |
| JP | 2016-179115 A | 10/2016 |

* cited by examiner

PARTICLE BEAM TRANSPORT APPARATUS, ROTARY GANTRY, AND PARTICLE BEAM IRRADIATION TREATMENT SYSTEM

Embodiments of the present invention relate to a particle beam treatment technique to treat an affected area by irradiating the affected area with a particle beam.

BACKGROUND

There has been increasing interest on a particle beam treatment technique in which treatment is performed by irradiating cancer cells of a patient with a particle beam such as a heavy particle ion beam.

The particle beam treatment technique make it possible to destroy the pinpoint affected area without damaging the normal tissues, which makes the burden on the patient small compared with surgery, medication therapy, or the like. Accordingly, the early comeback of the patient to society after the treatment will be also expected.

In order to irradiate the affected area with a particle beam that has the optimum dosage value and dose distribution depending on the shape of the affected area and its target depth from the body surface, a rotation method of rotating an irradiator with a rotary gantry has been attracting attention in recent years.

In order to support a particle beam transport apparatus stably with a rotary gantry, the particle beam transport apparatus is connected to the irradiator so as to meander into and out of the rotary gantry. The particle beam transport apparatus leads the particle beam to the irradiator.

PRIOR ART DOCUMENT

Patent Document

[Patent Document 1] Japanese Unexamined Patent Application Publication JP2011-72717A

SUMMARY OF THE INVENTION

Problem to be Solved by the Invention

Since various electromagnets and monitors for controlling the trajectory of the particle beam are provided in the beam transport path, the beam transport apparatus becomes complicated and longer.

For this reason, in the conventional technique, there is a possibility that the rotary gantry for supporting the beam transport apparatus is enlarged to deteriorate controllability of rotation and thereby its irradiation accuracy of the particle beam is reduced.

In view of the above-described problem, an object of embodiments of the present invention is to provide a particle beam transport apparatus, a rotary gantry, and a particle beam irradiation treatment system, in each of which the beam transport path is simplified and shortened.

Means for Solving Problem

A particle beam transport apparatus according to the present invention includes a vacuum duct, at least one magnet controller, and a scanning magnet. The vacuum duct is configured such that a particle beam advances through the vacuum duct. The magnet controller is disposed around a bent portion of the vacuum duct and is configured to control an advancing direction or shape of the particle beam. The scanning magnet is disposed on the downstream side of the magnet controller in the advancing direction and is configured to scan the particle beam by deflecting each bunch of the particle beam. The magnet controller includes a deflection magnet configured to deflect the advancing direction of the particle beam along the bent portion and a quadrupole magnet configured to converge the particle beam. The deflection magnet and the quadrupole magnet constitute a combined-function magnet arranged at the same point in the advancing direction.

Preferably, the at least one magnet controller includes plural magnet controllers and the plural magnet controllers are configured to deflect the advancing direction of the particle beam along the bent portion in such a manner that at least two of the plural magnet controllers are the same in terms of the deflection angle.

More preferably, the at least one magnet controller includes plural magnet controllers and at least two of the plural magnet controllers are the same in terms of a diameter of the magnet controller constituted by the quadrupole magnet or the deflection magnet.

In another embodiment of the present invention, a particle beam transport apparatus includes a vacuum duct, a magnet controller, and a scanning magnet. The vacuum duct is configured such that a particle beam advances through the vacuum duct. The magnet controller is disposed around a bent portion of the vacuum duct and is configured to control an advancing direction or shape of the particle beam. The scanning magnet is disposed on the downstream side of the magnet controller in the advancing direction and is configured to scan the particle beam by deflecting each bunch of the particle beam. The magnet controller includes a deflection magnet configured to deflect the advancing direction of the particle beam along the bent portion and a quadrupole magnet configured to converge the particle beam. The magnet controller is a bisected unit magnet bisected into two halves in such a manner that the two halves are arranged mirror-symmetrically with each other.

Preferably, the scanning magnet includes: a first scanning magnet pair configured to generate a scanning magnetic field in a first direction perpendicular to the advancing direction; and a second scanning magnet pair configured to generate a scanning magnetic field in a second direction that is perpendicular to the advancing direction and the first direction, and the first and second scanning magnet pairs are arranged at the same point in the advancing direction.

Desirably, the magnet controller includes a superconducting magnet.

A rotary gantry according to the present embodiment is a rotary gantry equipped with the above-described particle beam transport apparatus.

A particle beam irradiation treatment system according to the present embodiment is a treatment system equipped with the above-described particle beam transport apparatus.

Effect of Invention

The present invention provides a particle beam transport apparatus, a rotary gantry, and a particle beam irradiation treatment system, in each of which the beam transport path is simplified and shortened.

DESCRIPTION OF EMBODIMENTS

Hereinbelow, embodiments of the present invention will be described by referring to the accompanying drawings.

In each figure and each embodiment described below, the advancing direction of a particle beam β (hereinafter simply referred to as "the beam β") is defined as the S direction, the direction orthogonal to the S direction is defined as the X direction, and the direction orthogonal to both of the S direction and the X direction is defined as the Y direction.

First, a description will be given of a particle beam irradiation treatment system 100 by referring to FIG. 1.

Figure 1:
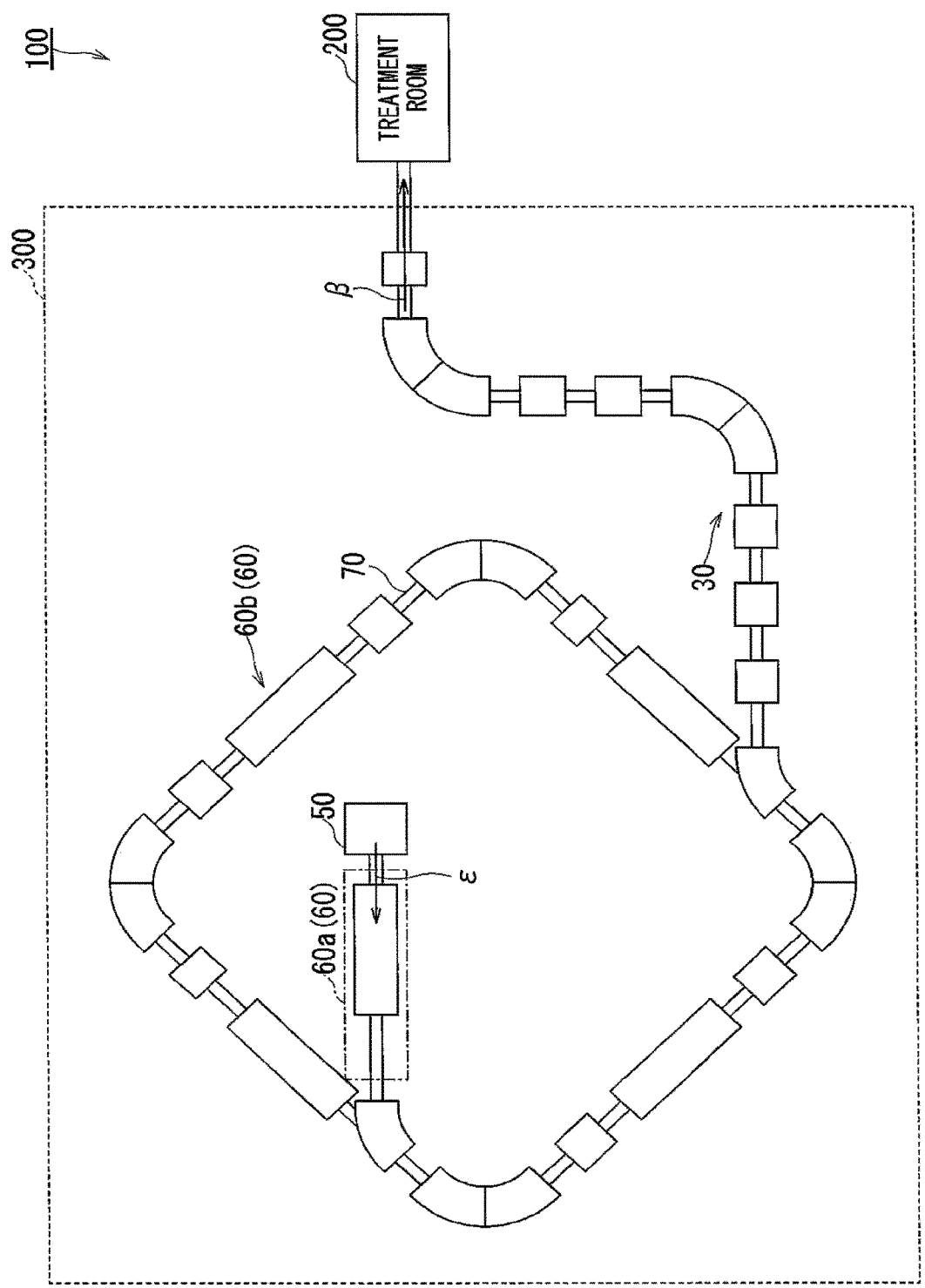
FIG. 1 is a schematic configuration diagram of a particle beam irradiation treatment system.

FIG. 1 is a schematic configuration diagram of the particle beam irradiation treatment system 100.

As shown in FIG. 1, the main components of the particle beam irradiation treatment system 100 are a treatment room 200 and an accelerator 300.

A group of heavy particle ions ε such as carbon ions accelerated by the accelerator 300 is led to the treatment room 200 and radiated onto the affected area of a patient P.

The main components of the accelerator 300 are an ion generator 50, an accelerator 60 (i.e., a linear accelerator 60a and a synchrotron accelerator 60b), and a particle beam transport apparatus (i.e., transport system) 30 (hereinafter simply referred to as the transport apparatus 30).

The heavy particle ions ε generated by the ion generator 50 are accelerated to about 70% of the light speed so as to become the beam β while circulating inside the accelerator 60 for about one million times, and then the beam β is led to the treatment room 200 by way of the transport apparatus 30.

Inside the accelerator 300, a vacuum duct (i.e., beam pipe) 70 is provided, and the beam β advances inside this vacuum duct 70. The linear accelerator 60a, the synchrotron accelerator 60b, and the vacuum duct 70 of the transport apparatus 30 integrally form a continuous space and constitute a beam transport path for leading the beam β from the ion generator 50 to the treatment room 200.

First Embodiment

Figure 2:
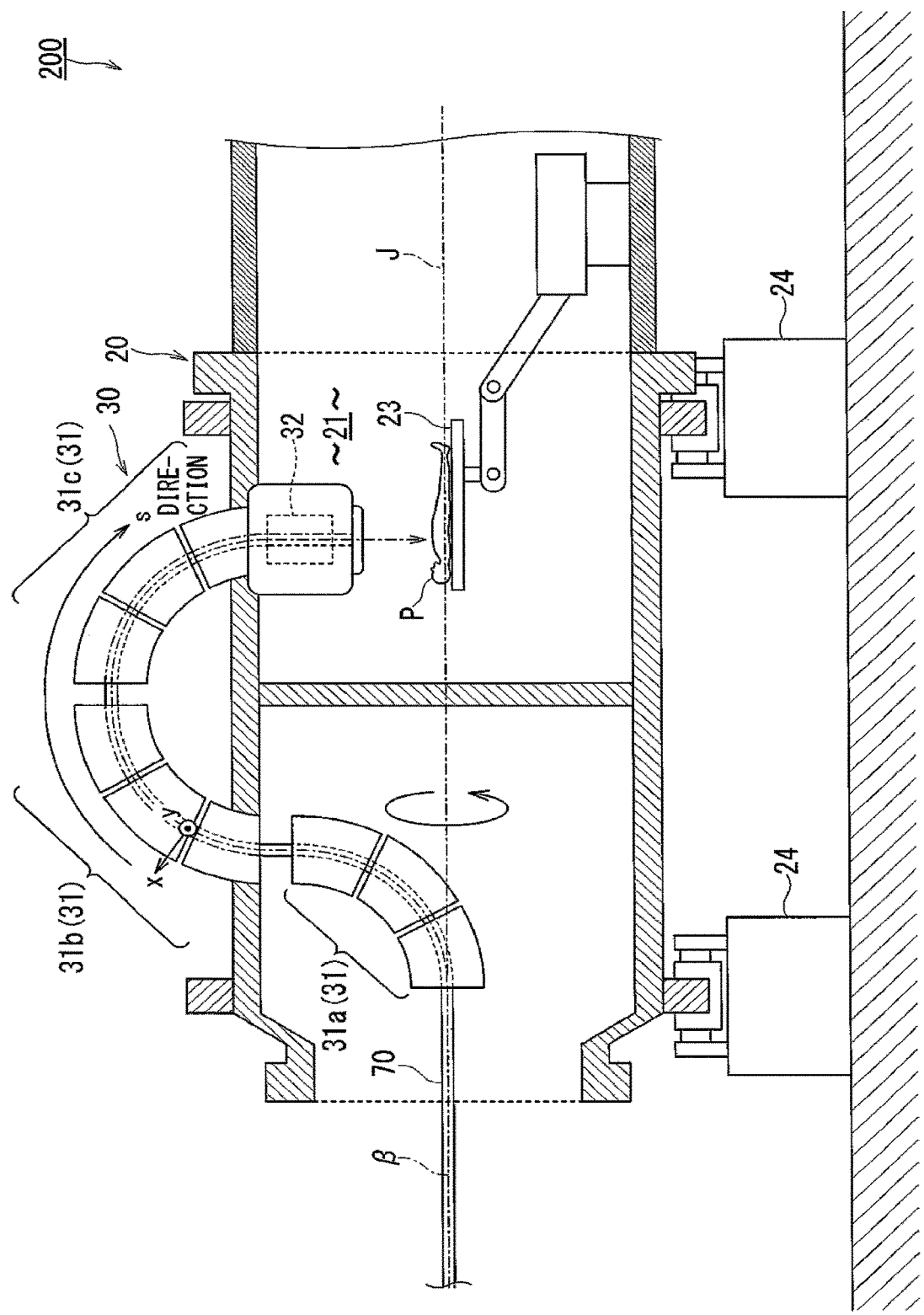
FIG. 2 is a schematic cross-sectional view of the surrounding of a treatment room equipped with the transport apparatus according to the first embodiment.

FIG. 2 is a schematic cross-sectional view of the treatment room 200 equipped with the transport apparatus 30 according to the first embodiment.

As shown in FIG. 2, the transport apparatus 30 is mounted and supported on the rotary gantry 20.

The rotary gantry 20 is a cylindrical apparatus installed on the foundation 24 such that its rotation axis (i.e., cylinder center) J extends in the horizontal direction. The inner space of the rotary gantry 20 constitutes a treatment space 21.

In the treatment space 21, a treatment table 23 is installed such that the patient P is positioned on the rotation axis J.

In order for the rotary gantry 20 to stably support the transport apparatus 30, the transport apparatus 30 enters the inside of the rotary gantry 20 along the rotation axis J, bends, once protrudes from the side wall of the rotary gantry 20 to the outside, and again enters the internal space on the side of the treatment space 21 so as to be fixed thereto.

At each part of the transport apparatus 30, magnet controllers 31 (31a to 31c) for controlling the advancing direction or shape of the beam β are disposed.

Next, the transport apparatus 30 according to the first embodiment will be described with continued reference to FIG. 2.

In the transport apparatus 30 according to the first embodiment, a scanning magnet 32 configured to deflect each bunch of the beams β and scan the beam β is disposed on the downstream side of the magnet controllers 31 in the S direction.

The scanning magnet 32 deflects the incoming heavy particle ions ε in units of bunches such that each bunch is radiated onto an appropriate position in the affected area.

Since the scanning magnet 32 scans the beam β in units of bunches, the cross-sectional shape of the beam β in an XY plane is expanded to the shape of the affected area as a whole.

As illustrated in FIG. 2, the magnet controllers 31 are generally provided at the respective three bent portions in the beam transport path that meanders around the supporting points by the rotary gantry 20.

For the sake of convenience, the magnet controllers 31 will be referred to as the first magnet controller 31a, the second magnet controller 31b, and the third controller 31c in order from the upstream side in the S direction.

The magnet controllers 31 deflects the beam β along the beam transport path in such a manner that all the magnet controllers 31 (31a to 31c) have the same deflection angle. In the following description, the deflection angle is assumed to be 90° as one case.

The scanning magnet 32 is disposed on the downstream of all the magnet controllers 31 (31a to 31c) in the S direction.

On the downstream side of the scanning magnet 32, for instance, a beam monitor for checking the properties of the beam β, filters such as a ridge filter, and a beam window are appropriately arranged.

In the conventional technique, the scanning magnet is placed between the second magnet controller 31b and the third magnet controller 31c. In this arrangement, the trajectory of the beam β is parallel to the rotation axis J of the rotary gantry 20, and consequently, the long side of the scanning magnet becomes parallel to the rotation axis J.

Contrastively, in the transport apparatus 30 according to the first embodiment, the scanning magnet 32 is at the position where the trajectory of the beam β is perpendicular to the rotation axis J.

In other words, since the long side of the scanning magnet 32 which used to be substantially horizontal is rotated by a quarter so as to be substantially vertical, the occupied length of the transport apparatus 30 can get shorten in the direction along the rotation axis J.

Further, when the treatment space 21 is large, the downstream side of the third magnet controller 31c in the S direction can be arranged so as to protrude into the treatment space 21 together with the scanning magnet 32 as shown in FIG. 2.

In this case, the occupied length of the transport apparatus 30 in the direction along the rotation axis J can be shortened without increasing the rotation radius of the transport apparatus 30.

Thus, in either case, the rotary gantry 20 for supporting the magnet controllers 31 can be made smaller and lighter.

Since the diameter of the beam β is increased by scanning with the use of the scanning magnet 32, in the conventional technique, the third the magnet controller 31c on the downstream side needs to have a large aperture together with the vacuum duct 70 at this portion.

Additionally, as the aperture becomes larger, the third the magnet controller 31c becomes larger and the distance between the magnets inside becomes larger, which reduces generation efficiency of a magnetic field.

However, in the transport apparatus 30 according to the first embodiment, the scanning magnet 32 is disposed on the downstream side of the third magnet controller 31c, and thus the third magnet controller 31c can be made compact and have high generation efficiency of a magnetic field.

Further, it is not necessary to enlarge the aperture of the third the magnet controller 31c. Thus, when the plural magnet controllers 31 with the same deflection angle are provided in the beam transport path, the number of identical products increases and the production efficiency can be improved.

The aperture of each magnet controllers 31 is defined by the distance of the pair of magnets facing to each other (i.e., the pair of quadrupole magnets facing each other or the pair of deflection magnets facing each other), which are arranged at the innermost layer (i.e., the position close to the vacuum duct 70).

In addition, when the magnet controllers 31 are configured to have different deflection angles that are a combination of values obtained by dividing 90° by a natural number such as 45° or 30°, the first, second, and third magnet controllers 31a, 31b, and 31c can be the identical products, and the production efficiency can be improved.

Further, the beam transport path is normally composed of three bending portions. Hence, when the deflection angle is set to 90°, it is possible to standardize the magnet controllers 31 on the same product and minimize the number of products, which further improves the production efficiency.

According to the transport apparatus 30 of the first embodiment as described above, it is possible to shorten the beam transport path in the direction of the rotation axis J.

Additionally, since the transport apparatus 30 is shortened, the rotary gantry 20 can be made smaller and lighter.

Further, since the identical products can be used for the magnet controllers 31 (31a to 31c) in a standardized manner, the structure is simplified and the production efficiency can be improved.

Second Embodiment

Figure 3:
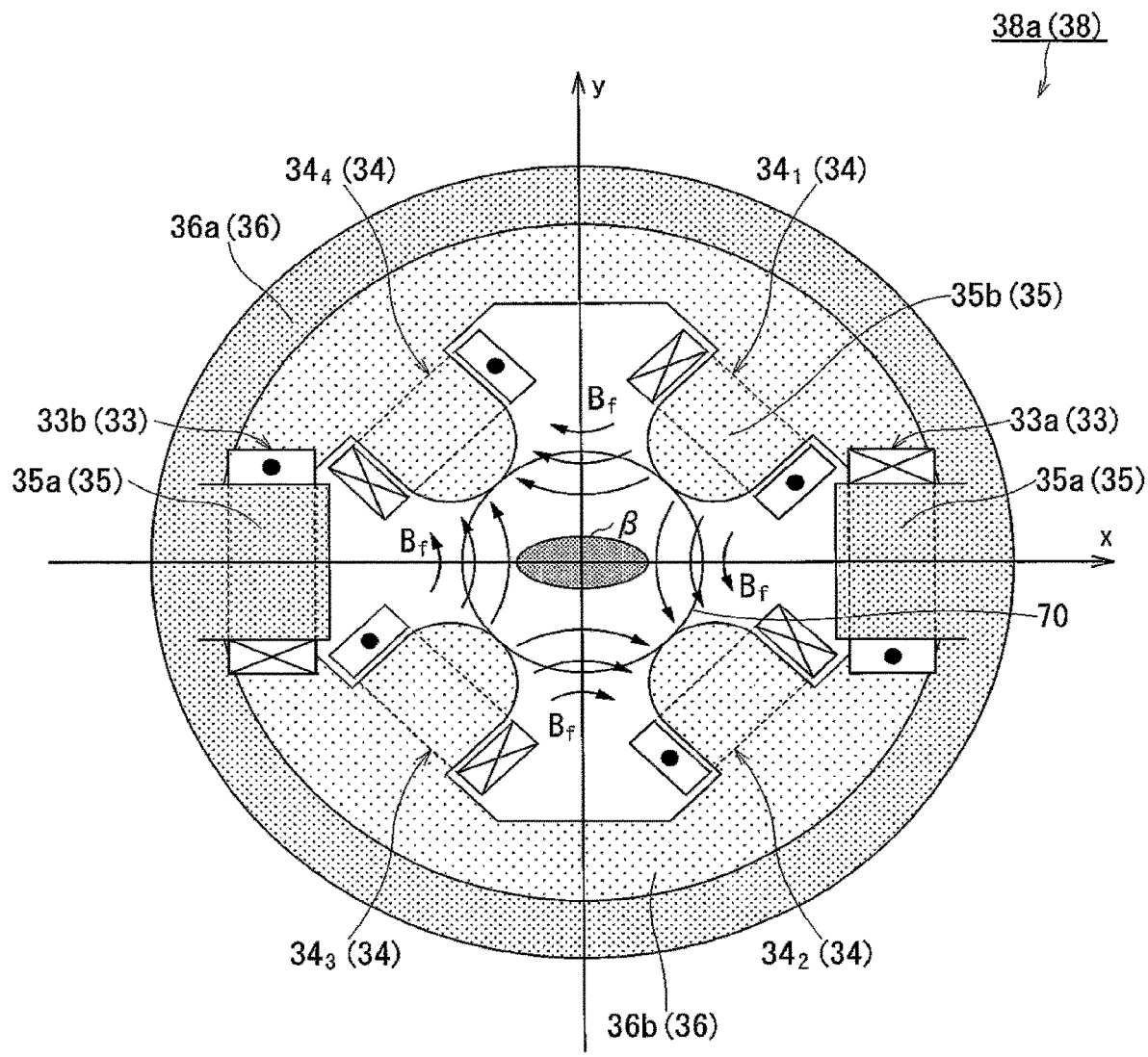
FIG. 3 is a schematic cross-sectional view of an XY plane of a combined-function magnet included in the transport apparatus according to the second embodiment.

FIG. 3 is a schematic cross-sectional view of an XY plane of the combined-function magnet 38 (38a) included in the transport apparatus 30 according to the second embodiment.

As shown in FIG. 3, the transport apparatus 30 according to the second embodiment includes a combined-function magnet 38 as a the magnet controller 31 that exhibits the function of deflecting the beam β and the function of controlling convergence and divergence of the beam β at the same position.

In many cases, each magnet controller 31 is composed of a deflection magnet 33 and a quadrupole magnet 34.

The quadrupole magnet 34 controls the convergence and divergence of the beam β. That is, the quadrupole magnet 34 controls the shape of the beam β in the cross-section (cross-section in the XY plane) perpendicular to the S direction.

The deflection magnet 33 is disposed at the bent portion of the vacuum duct 70, and generates a deflection magnetic field so as to deflect the beam β along the curvature of the bent portion.

Normally, the deflection magnet 33 is composed of two deflection coils 33a and 33b facing each other, but the deflection magnet 33 may be composed of coils other than two.

The combined-function magnet 38 can be realized by the quadrupole magnet 34 and the deflection magnet 33 each outputting the magnetic field shapes at the same point in the S direction.

Hereinafter, the combined-function magnet 38 will be described more specifically.

In the quadrupole magnet 34, normally, four excitation coils for shaping $34_1$ to $34_4$ are arranged on the circumference of the vacuum duct 70 in line symmetry with respect to the axis that is the trajectory of the beam β.

When the excitation coils for shaping $34_1$ to $34_4$ are excited, the quadrupole magnetic field Bf is generated in the internal gap of the vacuum duct 70.

The quadrupole magnet 34 shown in FIG. 3 diverges the beam β in the X direction and converges it in the Y direction by the Lorentz force that acts on each heavy particle ion.

Three sets—for instance—of the quadrupole magnets 34 are arranged along the S direction to form one magnet controller 31 (e.g., the first magnet controller 31a).

The quadrupole magnetic field Bf generated in each quadrupole magnet 34 is oppositely oriented with that of the adjacent quadrupole magnets 34 by reversing the direction of the direct current to each other.

Since the directions of the respective quadrupole magnetic fields Bf are made to be opposite to each other by the respective quadrupole magnets 34, the cross-section of the beam β is shaped by repeating convergence and divergence in the X direction and in the Y direction.

In FIG. 3, in order to simplify the description, the deflection magnetic fields generated by the deflection magnets 33 are not shown. The actual magnetic field is the superposition of the quadrupole magnetic fields Bf and the deflection magnetic fields.

Although the quadrupole magnet 34 composed of the four excitation coils for shaping $34_1$ to $34_4$ is shown as one case, the number of the excitation coils and the number of poles may be four or more.

For each deflection magnet 33 and each quadrupole magnet 34 using the normal conduction coil, the magnetic poles 35 (35a and 35 b) are provided in the return yokes 36 (36a and 36b) constituting the iron core to design the magnetic field shape.

In the conventional technique, the quadrupole magnet 34 and the deflection magnet 33 are not concentrically arranged but are shifted forward or backward in the S direction. Thus, the length of each magnet controller 31 becomes longer, and the length of the transport apparatus 30 becomes longer as the result.

However, in the second embodiment, for instance, the iron core (i.e., the return yokes 36 and the magnetic poles) of the portion which interferes with the arrangement is removed or the iron core is enlarged. In this manner, the quadrupole magnet 34 and the deflection magnet 33 are arranged concentrically around the trajectory of the beam β at the same point in the S direction.

Since the quadrupole magnet 34 and the deflection magnet 33 are arranged at the same point in the S direction, it is possible to realize the combined-function magnet 38 that shapes and deflects the beam β at the same point.

Accordingly, each magnet controller 31 is shortened. Consequently, in the transport apparatus 30, the portion supported by the rotary gantry 20 can be shortened in the direction of the rotation axis J, similarly to the effect of the first embodiment.

In the combined-function magnet 38, it is preferable to use a superconducting magnet for the respective constituent magnets 33 and 34. The combined-function magnet 38 using the superconducting magnet will be described in the third embodiment.

As long as the combined-function magnet 38 has the shaping function and the deflection function of the beam β, the exciting coils do not need to be clearly distinguished between the quadrupole magnet 34 and the deflection magnet 33.

Since the second embodiment has the same configuration and operation procedure as the first embodiment except that the combined-function magnet 38 is used, duplicate description is omitted.

In each figure, the same reference signs are used for the components having the same configuration or function, and duplicate description is omitted.

According to the transport apparatus 30 of the second embodiment as described above, since each magnet controller 31 can be shortened, the transport apparatus 30 can be further shortened in addition to that the effects of the first embodiment.

Third Embodiment

Figure 4:
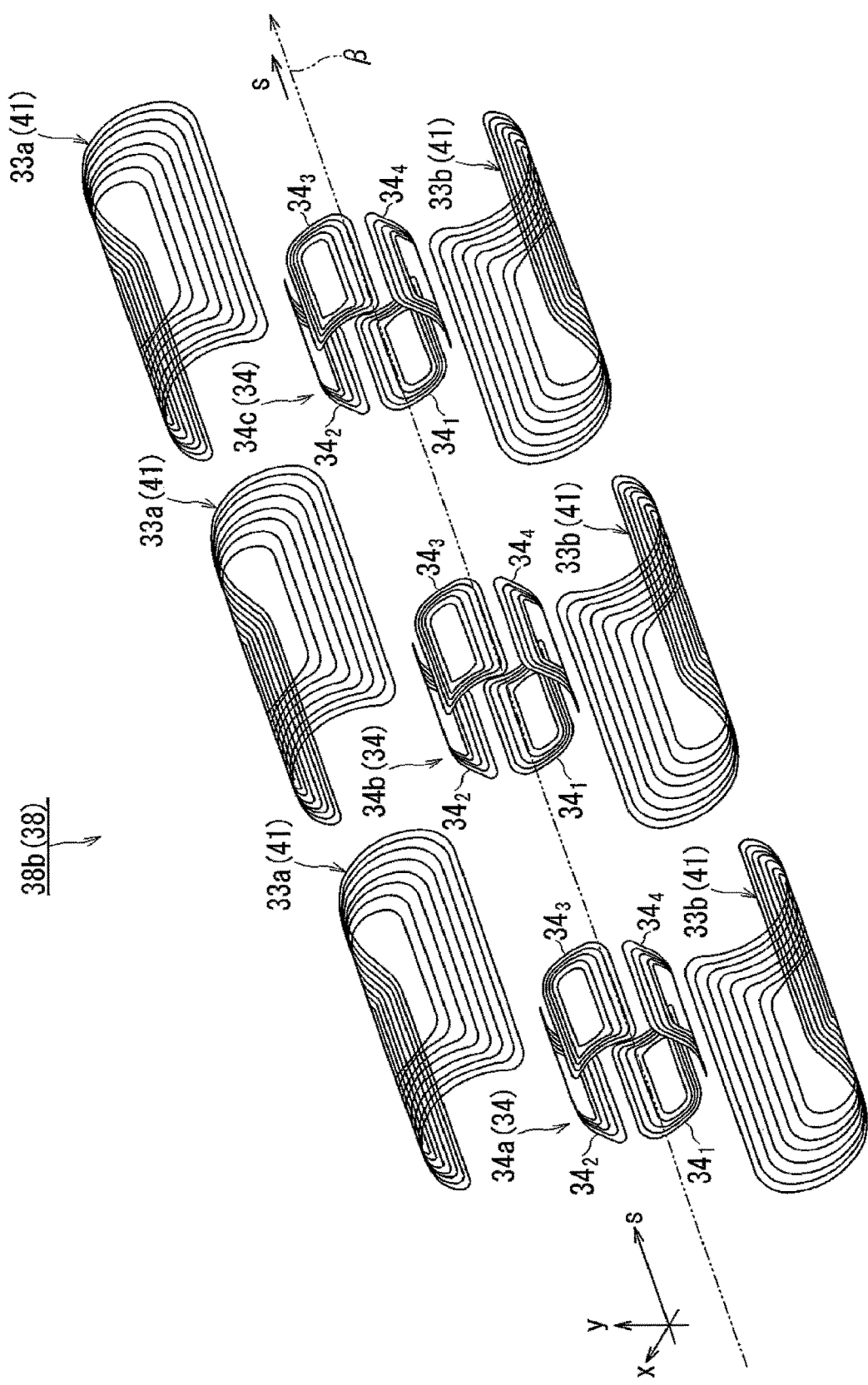
FIG. 4 is an exploded view of a state in which a group of superconducting coils constituting the magnet controllers of the transport apparatus according to the third embodiment are linearly expanded.

FIG. 4 is an exploded view illustrating a group of superconducting coils constituting the magnet controller 31 of the transport apparatus 30 according to the third embodiment.

Although the beam transport path is described as a straight line in FIG. 4 for simplifying the description, the actual beam transport path is curved and thus the superconducting coils are actually curved in accordance with the curve of the beam transport path.

Figure 5:
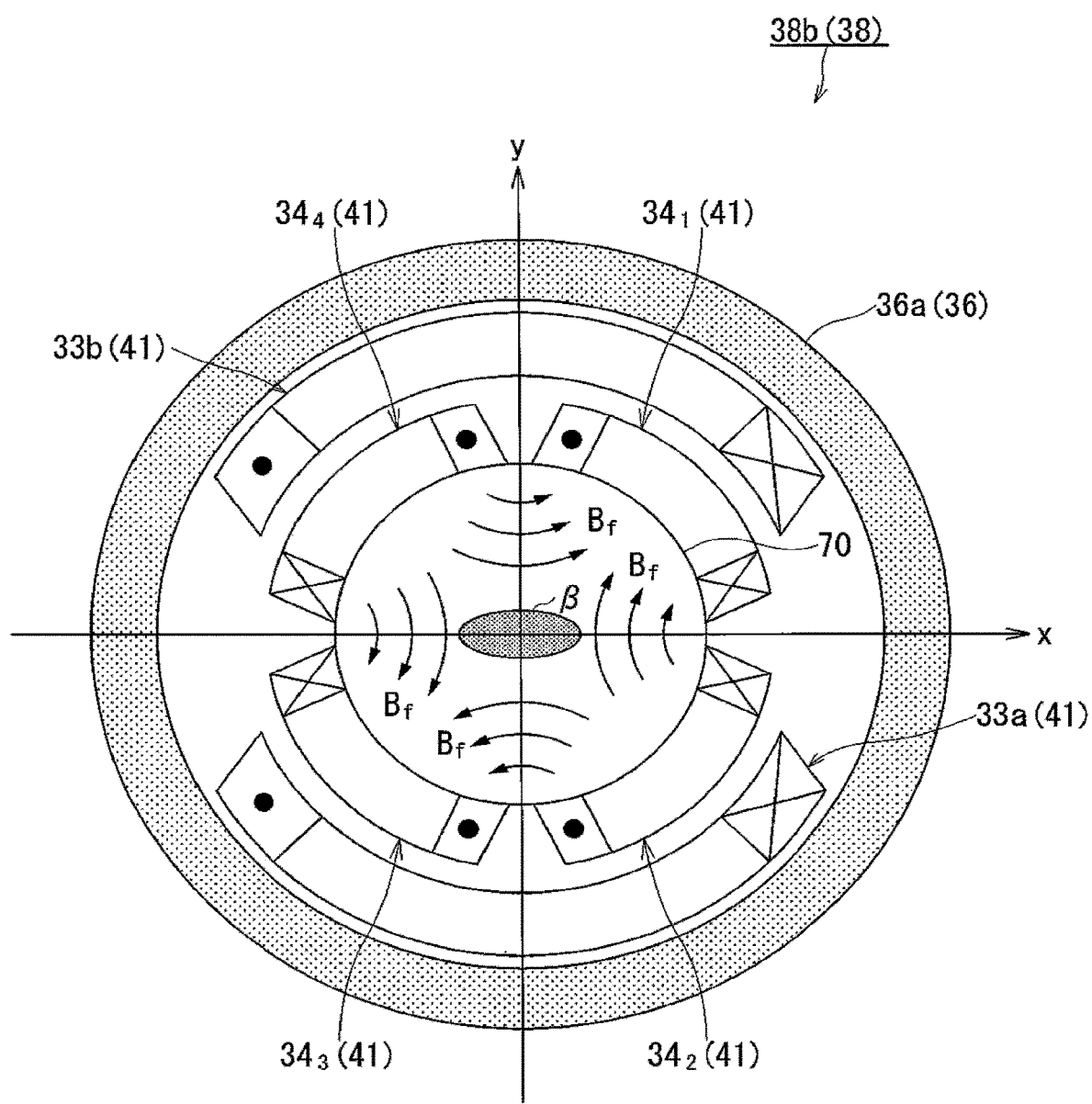
FIG. 5 is a schematic cross-sectional view of an XY plane of the transport apparatus according to the third embodiment.

FIG. 5 is a schematic cross-sectional view of an XY plane of the transport apparatus 30 according to the third embodiment.

In the transport apparatus 30 according to the third embodiment as shown in FIG. 4 and FIG. 5, at least a part of each magnet controller 31 is composed of a superconducting magnet. That is, the quadrupole magnet 34, the deflection magnet 33, the combined-function magnet 38 (38b), or at least one of these magnets is composed of a superconducting magnet.

When the scanning magnet 32 is disposed on the downstream side of the third magnet controller 31c, the rotation radius of the transport apparatus 30 may increase.

However, this rotation radius can be shortened by reducing the radius of curvature of the arrangement position of the magnet controller 31 in the beam transport path.

For this reason, in the third embodiment, the constituent magnets 33, 34, and 38 are composed of superconducting magnets, and a strong deflection magnetic field is generated to deflect the beam β with a small radius of curvature.

A superconducting coil is composed of a low-temperature superconductor such as NbTi, Nb3Sn, Nb3Al, and MgB2 or high-temperature superconductor such as Bi2Sr2Ca2Cu3O10 wire and REB2C3O7 wire. Here, "RE" in the "REB2C3O7" stands for rare earth element.

In the case of using the low-temperature superconductor, the low-temperature superconductor is rich in ductility and the above-described curved surface can be easily formed. In the case of using the high-temperature superconductor, the transition to the superconducting state occurs at high temperature, the cooling load is reduced, and the operation efficiency is improved.

In order to maintain the superconducting state, the constituent magnets 33, 34, and 38 are hermetically housed in a heat insulating container 39 together with a non-illustrated refrigeration medium.

The refrigeration medium is a liquid medium such as liquid nitrogen and liquid helium or a solid medium such as high purity aluminum that thermally conducts the cold heat supplied from the freezer to the constituent magnets 33, 34, and 38.

In the normal conductive coil, the magnetic poles 35 (35a and 35b) surround the respective surrounding spaces of the quadrupole magnets 34 and the deflection magnets 33 as shown in the second embodiment.

Thus, the magnetic poles 35 occupy the spaces, and the arrangement of the deflection magnets 33 with respect to the quadrupole magnets 34 cannot be freely designed.

However, in the case of using the superconducting magnets 41, normally, the shape of the magnetic field is formed without using the magnetic poles in the superconducting coil in view of magnetic saturation of iron or the like.

Hence, when the constituent magnets 33 and 34 are configured of the superconducting magnets 41, the constituent magnets 33 and 34 can be arranged concentrically at the same point in the S direction so as to form the combined-function magnet 38 (38b).

In other words, the deflection magnet 33 can be laminated on the outer periphery of the quadrupole magnet 34 by avoiding the use of magnetic poles, as shown in FIG. 5.

Figure 6:
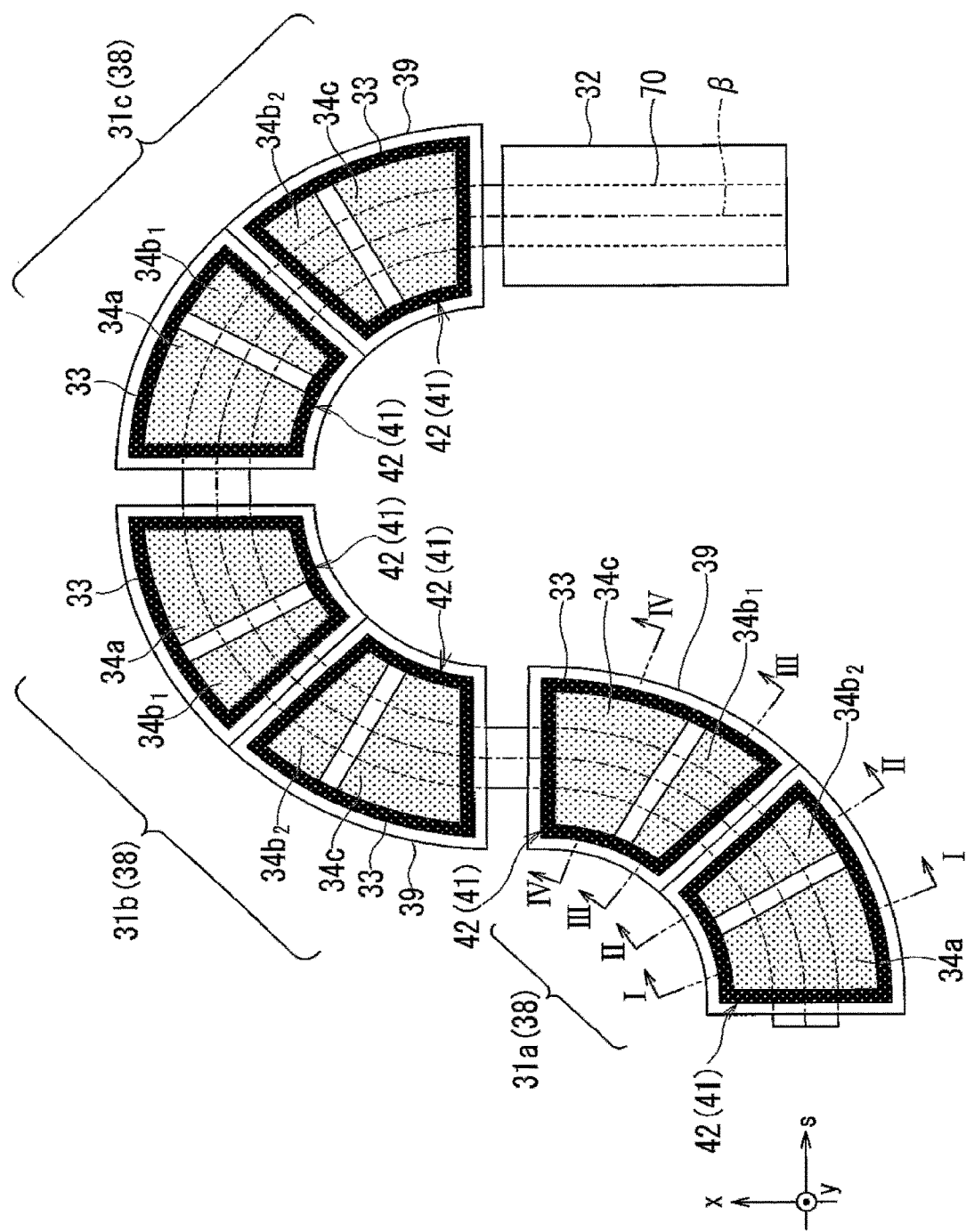
FIG. 6 is a schematic view illustrating a modification of the transport apparatus according to the third embodiment.

FIG. 6 is a schematic diagram illustrating a modification of the transport apparatus 30 according to the third embodiment.

Normally, in one magnet controller 31 (e.g., the first the magnet controller 31a), three quadrupole magnets 34 are arranged in series along the S direction such that the beam β is subjected to convergence, divergence, convergence in this order or subjected to divergence, convergence, divergence in this order. The three quadrupole magnets 34 are hereinafter referred to as the first quadrupole magnet 34a, the second quadrupole magnet 34b, and the third quadrupole magnet 34c in order from the upstream side in the S direction.

As described in the first embodiment, in order to produce the magnet controllers 31 efficiently, it is desirable to reduce number of types of the components by standardizing the components as much as possible.

From the viewpoint of preventing deviation of the arrangement position of the magnet controllers 31, it is also desirable to reduce the number of components of the magnet controllers 31.

For this reason, instead of configuring each magnet controller 31 with three unit magnets, the second quadrupole magnet 34b is configured as bisected unit magnets by equally dividing it into two halves of unit magnets that are arranged mirror-symmetrically with each other as shown in FIG. 6.

As a result, the length of the second quadrupole magnet 34b included in one bisected unit magnet 42 along the S direction becomes half as long as the length of the first quadrupole magnet 34a and the third quadrupole magnet 34c along the S direction.

Since the two second quadrupole magnets 34b (34$b_1$ and 34$b_2$) are subjected to the same arrangement such that the respective magnetic field distributions in the cross-sections II-II and III-III in FIG. 6 become the same, the second quadrupole magnet 34b maintains the function as one quadrupole magnet as a whole even when being divided and arranged.

Since the bisected unit magnets 42 of the same product are arranged mirror-symmetrically with each other, the cross-section I-I is the same as the cross-section IV-IV.

As described in the first embodiment, the same product can be used for the respective magnet controllers 31 (31a to 31c) by arranging the scanning magnet 32 on the downstream side of the third controller 31c.

In other words, it is possible to constitute all the magnet controllers 31 by combining one type of bisected unit magnets 42.

Since the third embodiment has the same configuration and operation procedure as the second embodiment except that a superconducting magnet is used for each magnet controller 31 and the combined-function magnet 38b is configured by using a superconducting magnet, duplicate description is omitted.

In each figure, the same reference signs are used for the components having the same configuration or function, and duplicate description is omitted.

According to the transport apparatus 30 of the third embodiment as described above, a large direct current can flow and thus the portion of the transport apparatus 30 to be mounted on the rotary gantry 20 can be reduced in size, in addition to that the effects of the second embodiment are obtained.

That is, it is possible to shorten the transport apparatus 30 both in the direction of the rotation axis J and in the direction of the rotation radius.

Further, the magnet controller 31 can be efficiently produced by combining two single bisected unit magnets 42 into one magnet controller 31.

Fourth Embodiment

Figure 7A:
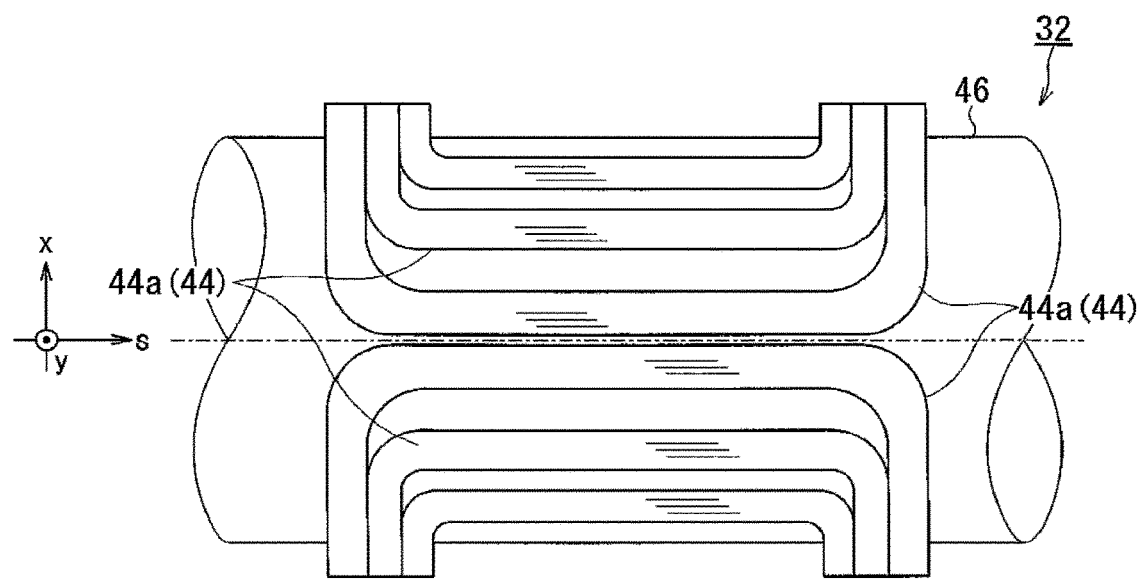
FIG. 7A is a side view of an X-direction scanning-magnet pair constituting the scanning magnet of the transport apparatus according to the fourth embodiment.
Figure 7B:
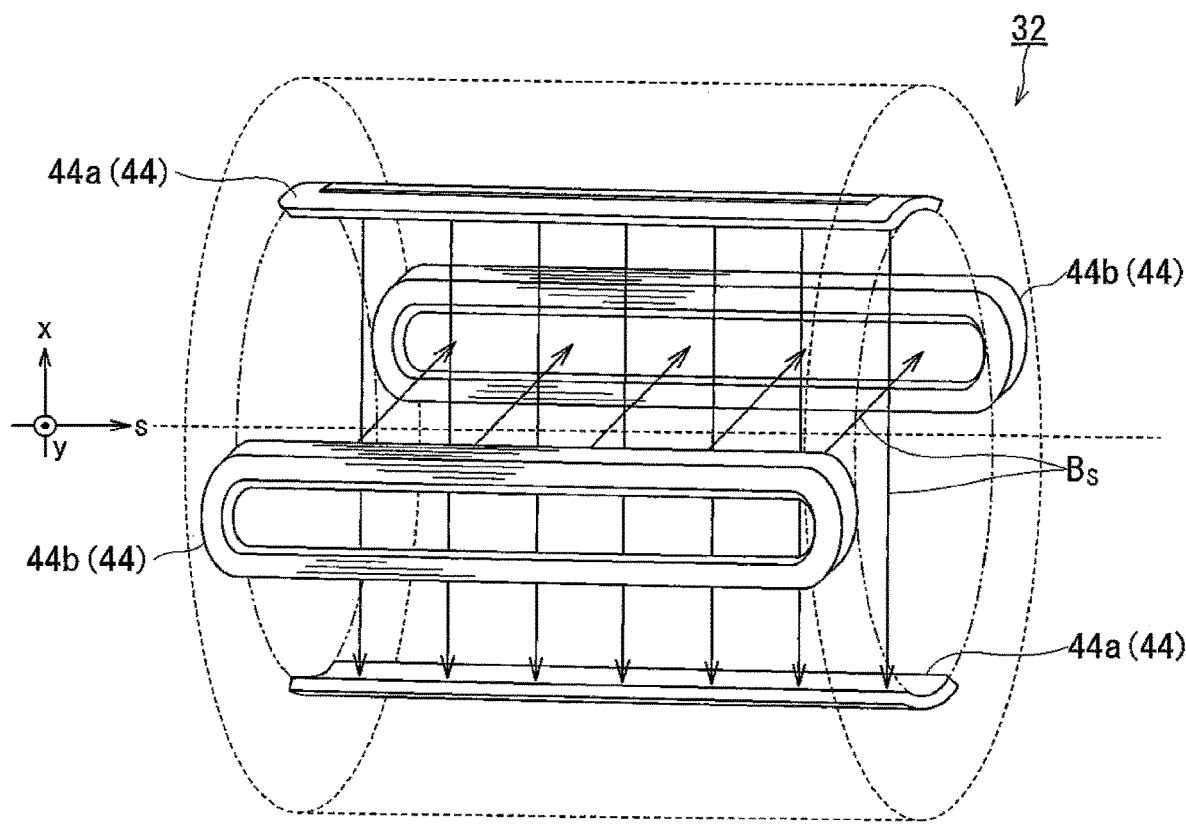
FIG. 7B is an exploded view illustrating the arrangement of the X-direction scanning-magnet pair and a Y-direction scanning-magnet pair.

FIG. 7A and FIG. 7B are schematic configuration diagrams of the scanning magnet 32 of the transport apparatus 30 according to the fourth embodiment.

FIG. 7A is a side view of an X-direction scanning-magnet pair (first scanning-magnet pair) 44a for scanning the beam β in the X direction.

FIG. 7B is an exploded view illustrating the arrangement of the X-direction scanning-magnet pair 44a and a Y-direction scanning-magnet pair (second scanning-magnet pair) 44b.

Although plural of the X-direction scanning-magnet pairs 44a and plural of the Y-direction scanning-magnet pairs 44b are included in general, only one pair of the X-direction scanning-magnets 44a and the Y-direction scanning-magnets 44b are illustrated in FIG. 7B in order to simplify the description.

In the transport apparatus 30 according to the fourth embodiment as shown in FIG. 7A and FIG. 7B, the scanning magnet 32 simultaneously scans the beam β at the same point of the S direction in the X direction and in the Y direction.

The scanning magnet 32 is composed of the X-direction scanning magnet pair 44a and the Y-direction scanning-magnet pair 44b.

The X-direction scanning-magnet pair 44a is provided along the Y-direction to face each other with the vacuum duct 70 interposed therebetween, and generates a scanning magnetic field Bs in the Y direction so as to scan the beam β in the X direction.

The Y-direction scanning-magnet pair 44b is provided along the X-direction to face each other with the vacuum duct 70 interposed therebetween, and generates a scanning magnetic field Bs in the X direction so as to scan the beam β in the Y direction.

In order to increase the strength of the magnetic field, plural pairs of the scanning magnets 44 are arranged concentrically.

Since the scanning magnet 32 is composed of an electromagnet similarly to the quadrupole magnet 34 and the like, the shape of the scanning magnetic field Bs in the conventional technique is adjusted by the shape of the magnetic pole.

Thus, in the conventional technique, the respective positions of the X-direction scanning-magnet pair 44a and the Y-direction scanning-magnet pair 44b are arranged in series so as to be shifted forward or backward in the S direction. For instance, in the conventional technique, the X-direction scanning-magnet pair 44a is arranged on the upstream side and the Y-direction scanning-magnet pair 44b is arranged on the downstream side.

However, the beam β spreads in the Y direction due to the scanning magnetic field Bs in the X direction. Thus, when the scanning magnet pairs 44 (44a and 44b) are arranged so as to be shifted in the S direction, the magnet-to-magnet distance of the Y-direction scanning-magnet pair 44b on the downstream side is widened. That is, when the X-direction scanning-magnet pair 44a scans the beam β widely, the aperture in the Y-direction scanning-magnet pair 44b increases.

Hence, when a large irradiation field is obtained in the Y direction by strengthening the scanning magnetic field Bs in the X direction, generation efficiency of the magnetic field in the Y direction decreases accordingly.

Thus, in order to obtain a sufficient irradiation field in the X direction, it is necessary to make the Y-direction scanning magnet pair 44b large in size.

Further, when the scanning magnet 32 is disposed at the most downstream position, increasing the size of the Y-direction scanning-magnet pair 44b may increase the rotation radius of the transport apparatus 30 by the rotation of the rotary gantry 20.

For this reason, in the fourth embodiment, the magnetic pole at the portion that hinders the arrangement is removed, and the X-direction scanning-magnet pair 44a and the Y-direction scanning-magnet pair 44b are concentrically arranged at the same position in the S direction.

The scanning magnet 32 composed of coils is shaped in a saddle shape, e.g., as shown in FIG. 7A so as to be arranged near the beam β without hindering the progression of the beam β.

The saddle shape is a shape in which the circular arc portion is curved so as to be non-coplanar with respect to the linear portion in so-called a track shape obtained by connecting two opposing circular arc portions of a coil at the linear portion.

This saddle-shaped coil is placed on the surface of a base 46 made of a material that does not generate an eddy current, such as a nonmagnetic metal surrounding the vacuum duct 70.

Further, the coils of the Y-direction scanning-magnet pair 44b are laminated on the outer side of the inner scanning-magnet pair 44 (e.g., the X-direction scanning-magnet pair 44a) while maintaining the insulating property.

The shape of the scanning magnet pair 44 is not limited to the saddle shape as long as it can keep the path of the beam β.

Since the fourth embodiment has the same configuration and operation procedure as the first embodiment except that the X-direction scanning-magnet pair 44a and the Y-direction scanning-magnet pair 44b are arranged at the same point in the S direction, duplicate description is omitted In each figure, the same reference signs are used for the components having the same configuration or function, and duplicate description is omitted.

According to the transport apparatus 30 of the fourth embodiment as described above, it is possible to shorten the distance from the scanning start point to the affected area keeping a sufficient irradiation field, in addition to that the effects of the first embodiment are obtained.

Further, it is possible to suppress increase in rotation radius of the transport apparatus 30 supported by the rotary gantry 20.

According to the transport apparatus 30 of at least one embodiment described above, it is possible to simplify and shorten the beam transport path by arranging the scanning magnet 32 on the downstream side of the third magnet controller 31c in the S direction.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For instance, among the respective portions of the transport apparatus 30, the portion mounted on the rotary gantry 20 may be manufactured integrally with the rotary gantry 20.

REFERENCE SIGNS LIST

100 . . . particle beam irradiation treatment system, 200 . . . treatment room, 300 . . . accelerator, 20 . . . rotary gantry, 21 . . . treatment space, 23 . . . treatment table, 24 . . . foundation, 30 . . . transport apparatus, 31 (31a-31c) . . . magnet controller (first magnet controller, second magnet controller, third magnet controller), 32 . . . scanning magnet, 33 . . . deflection magnet (constituent magnet), 33a, 33b (33) . . . deflection magnet, 34₁-34₄ (34) . . . excitation coil for shaping, 34 (34a-34c) . . . quadrupole magnet, 35 (35a, 35b) . . . magnetic pole, 36 (36a, 36b) . . . return yoke, 37 . . . superconducting coil, 38 (38a, 38b) . . . combined-function magnet (constituent magnet), 39 . . . heat insulating container, 41 . . . superconducting magnet, 42 . . . unit magnet, 44 (44a, 44b) . . . scanning magnet pair (x-direction scanning magnet pair, y-direction scanning magnet pair), 46 . . . base, 50 . . . ion generator, 60 (60a, 60b) . . . accelerator (linear accelerator, synchrotron accelerator), 70 . . . vacuum duct, $B_f$ . . . quadrupole magnetic field, $B_s$ . . . scanning magnetic field, J . . . rotation axis, P . . . patient, β . . . particle beam (beam), ε . . . heavy particle ion.

The invention claimed is:

1. A particle beam transport apparatus comprising:
   a vacuum duct through which a particle beam advances;
   at least one magnet controller disposed around a bent portion of the vacuum duct and configured to control an advancing direction or shape of the particle beam; and
   a scanning magnet disposed on a downstream side of the at least one magnet controller in the advancing direction of the particle beam and configured to scan the particle beam by deflecting each bunch of the particle beam,
   wherein the at least one magnet controller includes a deflection magnet configured to deflect the advancing direction of the particle beam along the bent portion and a quadrupole magnet configured to converge the particle beam; and
   the deflection magnet and the quadrupole magnet constitute a combined-function magnet arranged at a same point in the advancing direction of the particle beam.

2. The particle beam transport apparatus according to claim 1,
   wherein the at least one magnet controller comprises a plurality of magnet controllers; and
   wherein the plurality of magnet controllers are configured to deflect the advancing direction of the particle beam along the bent portion in such a manner that at least two of the plurality of magnet controllers are same in terms of a deflection angle of deflecting the advancing direction of the particle beam.

3. The particle beam transport apparatus according to claim 1,
   wherein the at least one magnet controller comprises a plurality of magnet controllers; and
   wherein at least two of the plurality of magnet controllers are same in terms of aperture of a magnet controller constituted by the quadrupole magnet or the deflection magnet.

4. The particle beam transport apparatus according to claim 1,
   wherein the scanning magnet comprises: a first scanning magnet pair configured to generate a scanning magnetic field in a first direction perpendicular to the advancing direction of the particle beam; and a second scanning magnet pair configured to generate a scanning magnetic field in a second direction that is perpendicular to the advancing direction of the particle beam and the first direction; and
   wherein the first scanning magnet pair and the second scanning magnet pair are arranged at a same point in the advancing direction of the particle beam.

5. The particle beam transport apparatus according to claim 1,
   wherein the at least one magnet controller includes a superconducting magnet.

6. A rotary gantry comprising the particle beam transport apparatus according claim 1.

7. A particle beam irradiation treatment system comprising the particle beam transport apparatus according to claim 1.

8. A particle beam transport apparatus comprising:
   a vacuum duct through which a particle beam advances;
   a magnet controller disposed around a bent portion of the vacuum duct and configured to control an advancing direction or shape of the particle beam; and a scanning magnet disposed on a downstream side of the magnet controller in the advancing direction of the particle beam and configured to scan the particle beam by deflecting each bunch of the particle beam, wherein the magnet controller includes a deflection magnet configured to deflect the advancing direction of the particle beam along the bent portion and a quadrupole magnet configured to converge the particle beam; and the magnet controller is configured as bisected unit magnets that are arranged mirror-symmetrically with each other.

* * * * *